US012629172B2

(12) United States Patent
Xu et al.

(10) Patent No.: US 12,629,172 B2
(45) Date of Patent: May 19, 2026

(54) SINGLE-PORT SURGICAL DEVICE AND MEDICAL DEVICE SYSTEM

(71) Applicant: BEIJING SURGERII ROBOTICS COMPANY LIMITED, Beijing (CN)

(72) Inventors: Kai Xu, Beijing (CN); Shu'an Zhang, Beijing (CN); Yitang Ren, Beijing (CN); Zhiren He, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 769 days.

(21) Appl. No.: 18/010,538

(22) PCT Filed: Jun. 15, 2021

(86) PCT No.: PCT/CN2021/099937
§ 371 (c)(1),
(2) Date: Dec. 15, 2022

(87) PCT Pub. No.: WO2022/017064
PCT Pub. Date: Jan. 27, 2022

(65) Prior Publication Data
US 2023/0240712 A1 Aug. 3, 2023

(30) Foreign Application Priority Data

Jul. 23, 2020 (CN) .......................... 202010716227.1
Aug. 19, 2020 (CN) .......................... 202010846093.5

(51) Int. Cl.
*A61B 17/34* (2006.01)
*A61B 34/30* (2016.01)
*A61B 17/00* (2006.01)

(52) U.S. Cl.
CPC .......... *A61B 17/3439* (2013.01); *A61B 34/30* (2016.02); *A61B 2017/00862* (2013.01);
(Continued)

(58) Field of Classification Search
CPC ............ A61B 17/3439; A61B 17/3421; A61B 17/00234; A61B 2017/3433;
(Continued)

(56) References Cited

U.S. PATENT DOCUMENTS

2003/0028179 A1 2/2003 Piskun
2004/0260246 A1 12/2004 Desmond
(Continued)

FOREIGN PATENT DOCUMENTS

CN 201492485 U 6/2010
CN 102596062 A 7/2012
(Continued)

OTHER PUBLICATIONS

Search Report in related Chinese Application No. 2020108350070, dated Mar. 10, 2025 (2 pages).
(Continued)

*Primary Examiner* — Jessica Weiss
(74) *Attorney, Agent, or Firm* — Bayes PLLC

(57) ABSTRACT

A single-port surgical device includes a housing and one or more cannulas. The housing includes a proximal port and a distal port, the one or more cannulas include an inner cannula section and an outer cannula section, the inner cannula section is located in the housing and communicates with the distal port of the housing, the outer cannula section is located outside the proximal port of the housing, and at least a portion of the outer cannula section of at least one cannula of the one or more cannulas is deformable in a radial direction, an axial direction or the radial direction and the axial direction of the outer cannula section.

16 Claims, 6 Drawing Sheets

(52) U.S. Cl.
CPC ................. *A61B 2017/3433* (2013.01); *A61B 2017/3441* (2013.01); *A61B 2017/3443* (2013.01); *A61B 2017/3447* (2013.01); *A61B 2034/302* (2016.02)

(58) Field of Classification Search
CPC .... A61B 2017/3443; A61B 2017/3441; A61B 2017/3447; A61B 2017/3445; A61B 2017/00862; A61B 2017/0034; A61B 34/30; A61B 2034/302
USPC ........................................................ 600/204
See application file for complete search history.

(56) References Cited

U.S. PATENT DOCUMENTS

| | | | |
|---|---|---|---|
| 2005/0096507 A1 | 5/2005 | Prosek | |
| 2009/0012477 A1* | 1/2009 | Norton | A61B 17/3423 604/174 |
| 2010/0234689 A1* | 9/2010 | Wagner | A61B 17/3421 600/210 |
| 2010/0249694 A1* | 9/2010 | Choi | A61B 17/0293 604/167.03 |
| 2011/0071359 A1* | 3/2011 | Bonadio | A61B 17/0293 600/184 |
| 2011/0160539 A1* | 6/2011 | Robertson | A61B 17/3421 600/204 |
| 2013/0041231 A1 | 2/2013 | Bonadio et al. | |
| 2015/0080931 A1* | 3/2015 | Piskun | A61B 1/32 606/185 |
| 2016/0074626 A1* | 3/2016 | Weadock | A61N 5/00 601/3 |
| 2019/0321115 A1* | 10/2019 | Anderson | A61B 34/20 |
| 2020/0022726 A1 | 1/2020 | Mikol et al. | |
| 2021/0338217 A1* | 11/2021 | Kojima | A61B 17/3423 |

FOREIGN PATENT DOCUMENTS

| | | | | |
|---|---|---|---|---|
| CN | 103085083 A | 5/2013 | | |
| CN | 103200860 A | 7/2013 | | |
| CN | 203263502 U | 11/2013 | | |
| CN | 106236267 A | 12/2016 | | |
| CN | 208002830 U | 10/2018 | | |
| CN | 209490097 U | 10/2019 | | |
| CN | 209916197 U | 1/2020 | | |
| CN | 210990440 U | 7/2020 | | |
| JP | 2008507334 A | 3/2008 | | |
| JP | 2010523172 A | 7/2010 | | |
| JP | 2011218171 A | 11/2011 | | |
| WO | WO-2010044051 A1 * | 4/2010 | ......... | A61B 17/3421 |
| WO | 2010082722 A1 | 7/2010 | | |
| WO | WO-2010112903 A1 * | 10/2010 | ......... | A61B 17/3423 |
| WO | WO-2012113509 A2 * | 8/2012 | ......... | A61B 17/3423 |
| WO | WO-2014026960 A2 * | 2/2014 | ........... | A61M 39/02 |
| WO | 2020123236 A1 | 6/2020 | | |

OTHER PUBLICATIONS

Office Action in related Canadian Application No. 3173645 dated Feb. 27, 2024 (4 pages).
Office Action in related Japanese Application No. 2022-580282 dated Dec. 26, 2023 (6 pages).
Search Report in related Chinese Application No. 202180005087.X dated Jan. 11, 2024 (2 pages).
International Search Report and Written Opinion in related PCT Application No. PCT/CN2021/099937 dated Sep. 22, 2021 (10 pages).
Extended European Search Report in related European Application No. 21847086.2 dated Jul. 17, 2024 (7 pages).

* cited by examiner

<u>100</u>
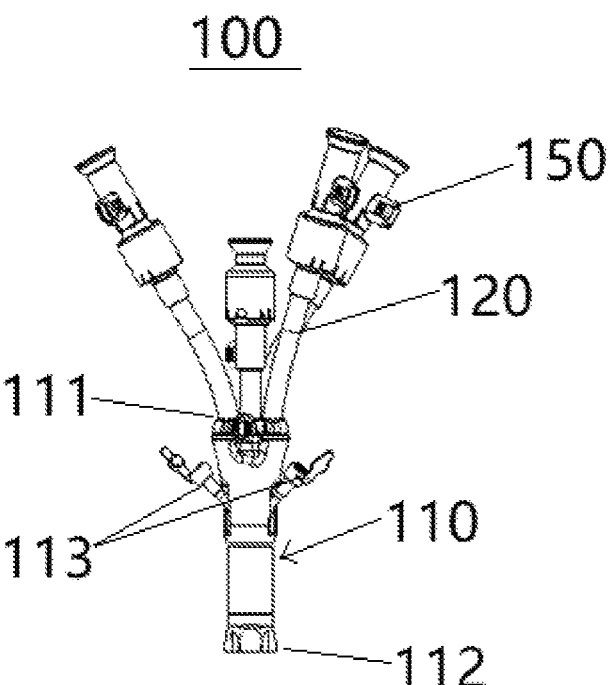
FIG.    1
<u>100</u>
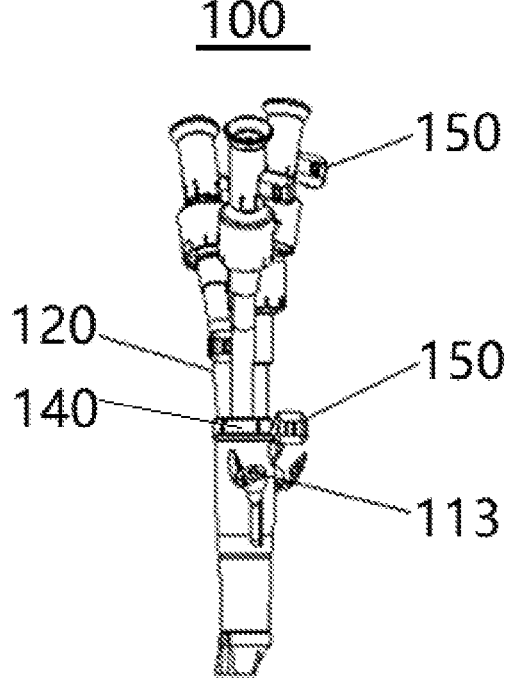
FIG.    2

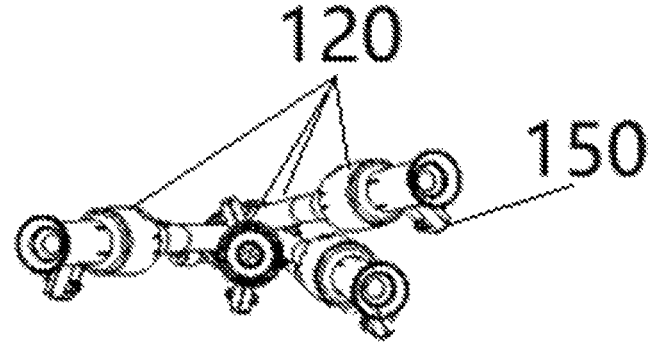
FIG.    3
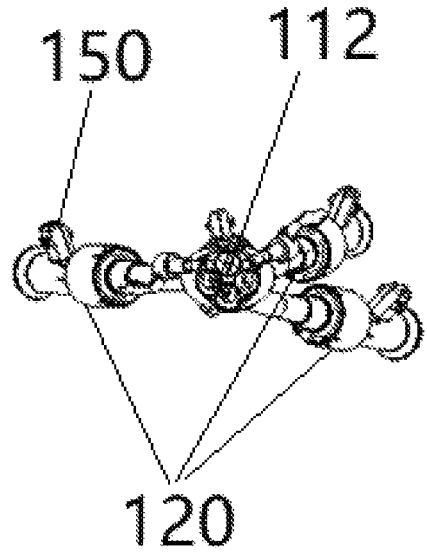
FIG.    4

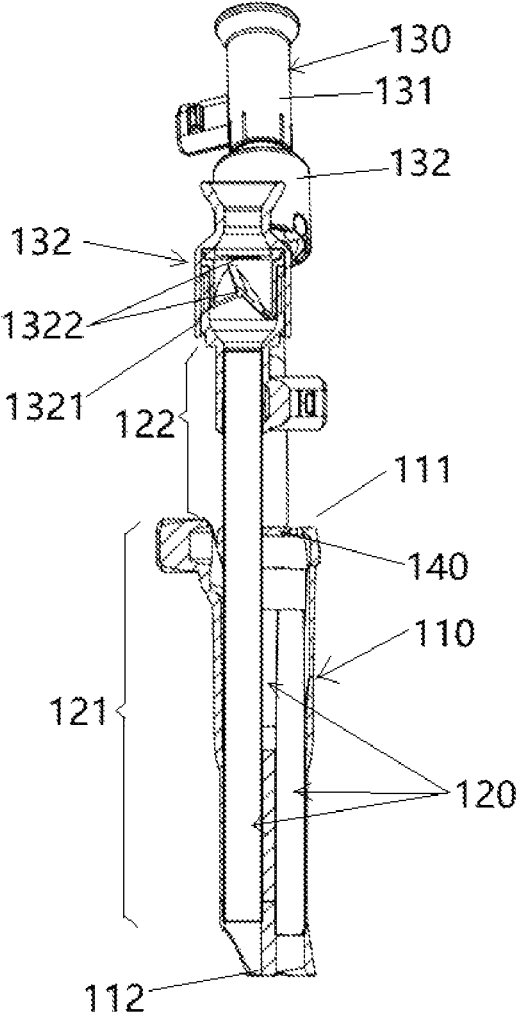
FIG.    5

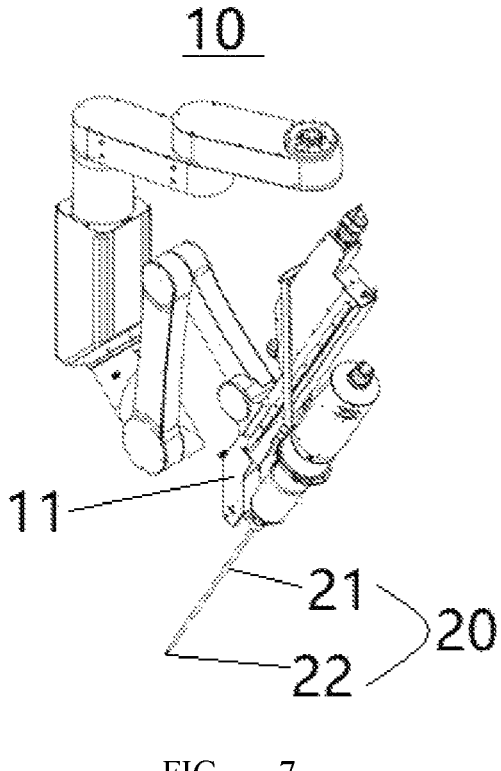
FIG.    7

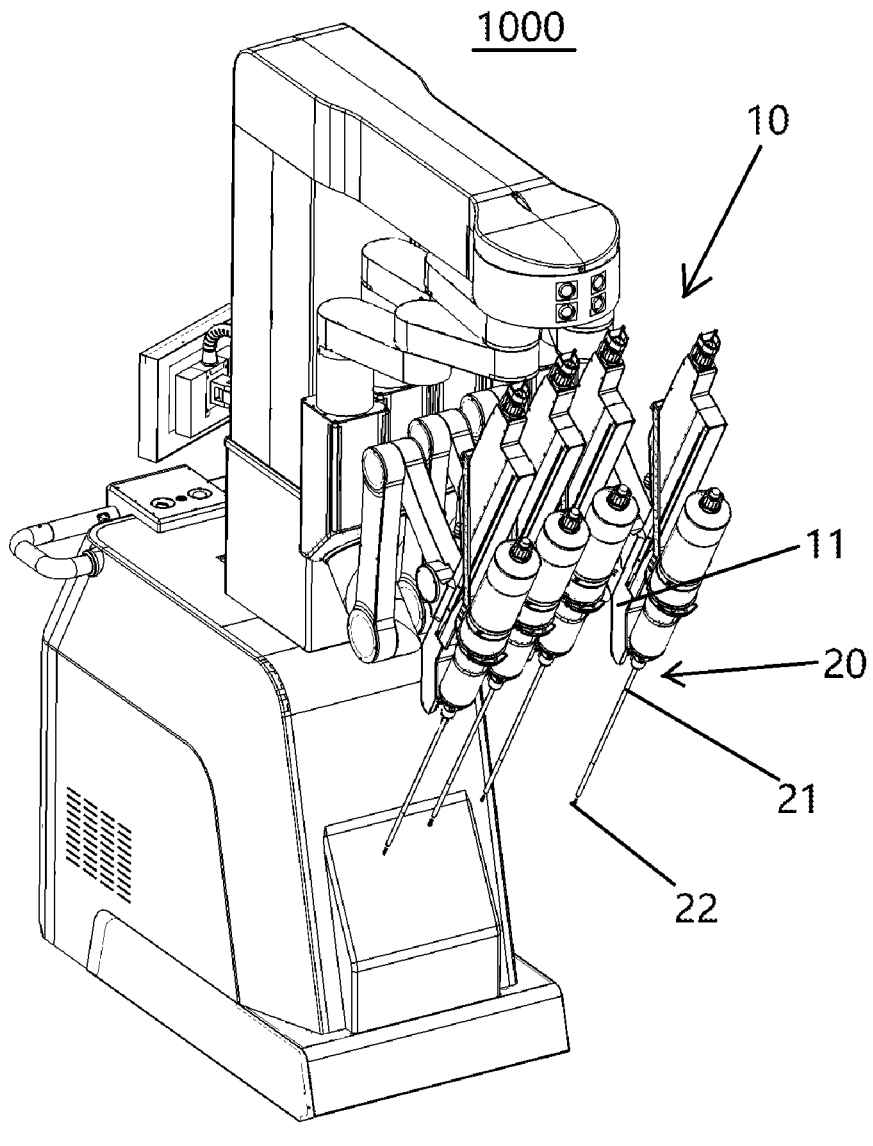
FIG.    8

SINGLE-PORT SURGICAL DEVICE AND MEDICAL DEVICE SYSTEM

CROSS-REFERENCE TO RELATED APPLICATIONS

The present application is a national stage of International Application No. PCT/CN2021/099937, filed on Jun. 15, 2021, which claims priority to Chinese Patent Application No. 202010846093.5, filed on Aug. 19, 2020 and Chinese Patent Applicant No. 202010716227.1, filed on Jul. 23, 2020. The entire contents of each of the above-identified applications are expressly incorporated herein by reference.

TECHNICAL FIELD

The present disclosure relates to the field of medical instruments, and in particular, to a single-port surgical device and a medical device system.

BACKGROUND

A single-port laparoscopic surgery is a surgical form that has been gradually developed and widely used in recent years, and has the advantages of a small wound, quick postoperative recovery, low postoperative infection and complications, etc. In the past two years, a batch of surgical robot products mainly from Intuitive surgical Co., Ltd. in the United States have optimized a surgical form by means of a technology for remote control using a computer, and achieved surgeries with higher stability and precision by means of mechanical arms. In a surgical process, a plurality of mechanical arms are placed into a human body by means of a sheath sleeve, and surgeries at different sites are implemented by controlling joints of the mechanical arms and an end surgical instrument.

At present, using a surgical robot to implement the surgical process mainly comprises three processes: preoperative preparation, surgical operation, and postoperative finishing. Before the surgery, a surgery assistant (usually an assistant doctor or a nurse practitioner) adjusts the mechanical arm to appropriate positions according to a surgical type and a surgical position, and a part of the sheath sleeve extends into a human body by means of a natural opening or a cutout, while the other part thereof is located outside the human body. The mechanical arm is fixedly connected to the part of the sheath sleeve outside the human body, and a surgical instrument with an end device at the end thereof is disposed on the mechanical arm, so that the end device enters, by means of the sheath sleeve, a corresponding position in the human body that needs a surgery. However, due to the limitation of motion control precision and motion angle of the mechanical arm itself, when entering the human body by means of the sheath sleeve, one or more end devices may not reach the relative position and the absolute position in a sheath sleeve design, so that a user needs to readjust the angle of each degree of freedom of the mechanical arm so that the end device can smoothly enter the sheath sleeve.

SUMMARY

In some embodiments, the present disclosure provides a single-port surgical device, comprising:

a housing comprising a proximal port and a distal port; and one or more cannulas comprising an inner cannula section and an outer cannula section, wherein the inner cannula section is located in the housing and communicates with the distal port of the housing, the outer cannula section is located outside the proximal port of the housing, and at least a portion of the outer cannula section of at least one cannula of the one or more cannulas is deformable in a radial direction, an axial direction or the radial direction and the axial direction of the outer cannula section.

In some embodiments, the present disclosure provides a medical device system, comprising: at least one motion arm comprising a plurality of arm bodies and a plurality of joints connecting the plurality of arm bodies; at least one surgical instrument disposed at the end of the at least one motion arm, the at least one surgical instrument comprising at least one end device disposed at the end of the at least one surgical instrument; a control system in communication connection with the at least one motion arm and configured to control the movement of the at least one motion arm; and a single-port surgical device comprising: a housing, the housing being tubular and comprising a proximal port and a distal port; and one or more cannulas for the at least one surgical instrument to pass through, the one or more cannulas comprising an inner cannula section and an outer cannula section, wherein the inner cannula section is located in the housing and communicates with the distal port of the housing, the outer cannula section is located outside the proximal port of the housing, and at least a portion of the outer cannula section of at least one cannula of the one or more cannulas is deformable in a radial direction, an axial direction or the radial direction and the axial direction of the outer cannula section.

BRIEF DESCRIPTION OF DRAWINGS

To illustrate technical solutions in embodiments of the present disclosure more clearly, the following briefly describes accompanying drawings required in the description of the embodiments of the present disclosure. The accompanying drawings in the following description show only some embodiments of the present disclosure, and those of ordinary skill in the art may further obtain other embodiments according to the content of the embodiments of the present disclosure and these accompanying drawings without creative efforts.

FIG. 1 is a schematic structural diagram of a single-port surgical device according to some embodiments of the present disclosure;

FIG. 2 is a left view of a single-port surgical device according to some embodiments of the present disclosure;

FIG. 3 is a top view of a single-port surgical device according to some embodiments of the present disclosure;

FIG. 4 is a bottom view of a single-port surgical device according to some embodiments of the present disclosure;

FIG. 5 is a partial sectional schematic structural diagram of a single-port surgical device according to some embodiments of the present disclosure;

FIG. 7 is a schematic structural diagram of a motion arm of a medical device system according to some embodiments of the present disclosure; and FIG. 8 is a schematic structural diagram of a medical device system according to some embodiments of the present disclosure.

DETAILED DESCRIPTION

Figure 6:
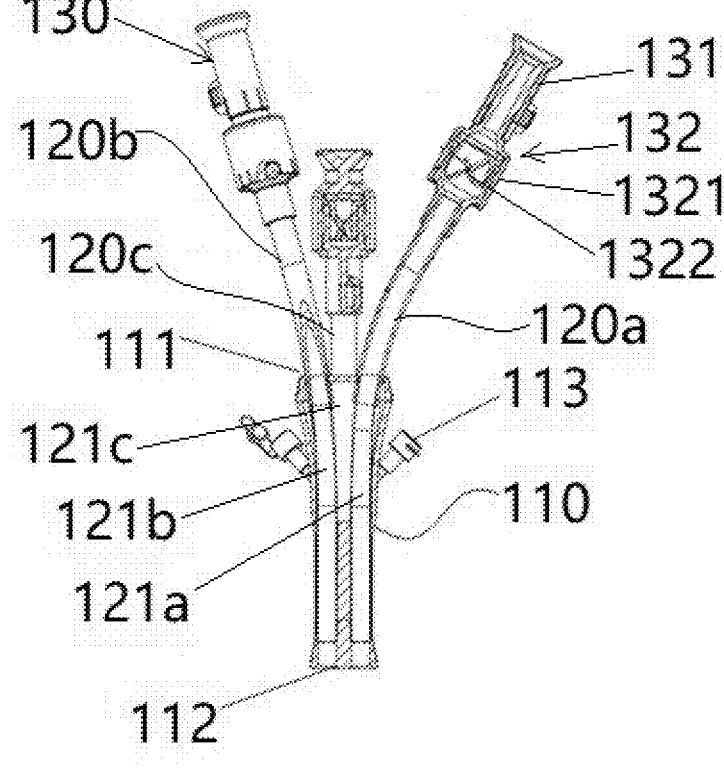
FIG. 6 is a partial sectional schematic structural diagram of a single-port surgical device according to some embodiments of the present disclosure at another angle.

To make the technical problems solved by the present disclosure, and the technical solutions used by the present disclosure and technical effects achieved by the present disclosure clearer, the technical solutions of the embodiments of the present disclosure will be further described in detail below with reference to the accompanying drawings. Obviously, the described embodiments are only exemplary embodiments of the present disclosure, but not all embodiments.

In descriptions of the present disclosure, it should be noted that, direction or position relationships indicated by terms "central", "upper", "lower", "left", "right", "vertical", "horizontal", "inner", "outer", and the like are direction or position relationships based on the accompanying drawings, and are merely intended to facilitate the descriptions of the present disclosure and simplify the descriptions, rather than indicating or implying that a referred device or element must have a particular direction or be constructed or operated in a particular direction. Therefore, these terms cannot be construed as limiting the present disclosure. In addition, the terms "first" and "second" are used for descriptive purposes only, and cannot be construed as indicating or implying relative importance. In the description of the present disclosure, it should be noted that, unless otherwise specified and defined, the term "mount", "connected", "connect", or "couple" should be comprehended in a broad sense. For example, the term may be a fixed connection or a detachable connection; or may be a mechanical connection or an electrical connection; or may be a direct connection, or an indirect connection by means of an intermediate medium; or may be internal communication between two elements. For those of ordinary skill in the art, specific meanings of the foregoing terms in the present disclosure may be understood based on specific situations. In the present disclosure, the end close to an operator (e.g., a doctor) is defined as a proximal end, a proximal portion, a rear end, or a rear portion, and the end close to a surgical patient is defined as a distal end, a distal portion, a front end, or a front portion. It may be understood by those skilled in the art that the embodiments of the present disclosure may be applied to a medical instrument or a surgical robot, or may also be applied to another non-medical device.

FIG. 1 is a schematic structural diagram of a single-port surgical device according to some embodiments of the present disclosure. As shown in FIG. 1, this embodiment provides a single-port surgical device 100, which may comprise a housing 110 and at least one cannula 120. FIGS. 2 to 5 respectively show a left view, a top view, a bottom view, and a partial sectional schematic structural diagram of a single-port surgical device 100 according to some embodiments of the present disclosure. In some embodiments, as shown in FIGS. 1 to 5, the housing 110 is tubular and may comprise a proximal port 111 (e.g., a bell mouth) and a distal port 112 (e.g., a contraction port). In some embodiments, the housing 110 is tubular, and may comprise a tapered proximal part (e.g., generally funnel-shaped or cone-shaped), and may comprise a proximal bell mouth and a distal contraction port. A tube wall is provided between the proximal port 111 and the distal port 112 for transition. A distal end of the at least one cannula 120 extends into the housing 110 and communicates with the distal port 112 of the housing 110, and a proximal end of the cannula extends out of the housing 110 from the proximal port 111. In some embodiments, the cannula 120 may comprise an inner cannula section 121 and an outer cannula section 122 (see FIG. 5) that communicate with each other, the inner cannula section 121 is located in the housing 110 and communicates with the distal port 112 of the housing 110, and the outer cannula section 122 is located outside the proximal port 111 of the housing 110. It may be understood that in some embodiments, the inner cannula section 121 may be a part of the housing 110 (e.g., the inner cannula section 121 may be an internal channel of the housing 110) or integrally formed with the housing 110, and the outer cannula section 122 communicates with the inner cannula section 121. At least a portion of the outer cannula section 122 is deformable, and the deformation includes a deformation (e.g., bending, extending or retracting, etc.) in a radial direction and/or an axial direction of the outer cannula section 122. In some embodiments, a part of the housing 110 close to the proximal port 111 may comprise an inner cavity, and a part of the housing 110 close to the distal port 112 may comprise a plurality of through channels disposed spaced apart from each other (a distal channel part close to the distal port 112 as shown), and the inner cannula section 121 of the at least one cannula 120 may be disposed in at least one through channel, or an end portion of the inner cannula section 121 of the at least one cannula 120 is fixedly connected to at least one through channel, so that the inner cannula section 121 communicates with the through channel.

The single-port surgical device 100 may be connected to a motion arm of a medical device system. Taking a motion arm 10 (see FIG. 7) as an example, the cannula 120 of the single-port surgical device 100 may be used for a surgical instrument 20 (e.g., a surgical tool or an endoscope) of the motion arm 10 to pass through, so as to enter a predetermined surgical site. In order to align with the cannula 120 of the single-port surgical device 100, the requirements for the positioning precision of the motion arm 10 are relatively high. For example, during preoperative preparation, a plurality of motion arms 10 need to move to appropriate positions to be automatically or manually connected to a plurality of cannulas 120. Or, during a surgery, it may be necessary to adjust the motion arm 10 as a whole along a fixed point (such as an abdominal entry point) to adjust the surgical field of view or the position and posture of the surgical instrument 20, etc., and the positional relationship between the motion arm 10 and the single-port surgical device 100 may be offset. Or, due to the limitation of the relative relationship between a plurality of surgical instruments 20 (for example, the distribution of cannulas 120 of the single-port surgical device 100, the interference between the surgical instruments 20 or the joint limit of the motion arm 10), the surgical instruments 20 may fail to reach a target position and posture according to an instruction of the system. Because the cannula 120 is deformable in the radial direction and/or the axial direction, the deformation can compensate for the positioning error or offset of the motion arm caused by machine control precision or another reason (including but not limited to the foregoing conditions), so that the end of the surgical instrument 20 can still relatively smoothly enter a predetermined surgical site by means of the cannula 120 and the inner cavity of the housing 110 even in the situation in which there is a certain positioning error or offset.

In some embodiments, the cannula 120 may comprise a plurality of tube sections made of different materials and distributed in a lengthwise direction, wherein at least a portion of the outer cannula section 122 of the cannula 120 is made of a flexible material. The flexible material enables the outer cannula section 122 of the cannula 120 to deform. Another material may be selected as a material of the remaining tube sections on the sheath 120 taking into account the cost or the diameter of a cannula or the optimization of contact with the motion arm. For example, the outer cannula section 122 may be made of a flexible material, while the inner cannula section 121 may be made of a non-flexible material. It should be understood that a part of the outer cannula section 122 may also be made of a flexible material while the other part thereof is made of a non-flexible material, and a part of the inner cannula section 121 may also be made of a flexible material, while the other part thereof is made of a non-flexible material. In some embodiments, the cannula 120 may also be made of a flexible material as a whole, so that the cannula 120 has a simple structure, and the flexibility of a deformation amount is high. In some embodiments, at least a portion of the inner cannula section 121 of the cannula 120 may be connected to an inner wall of the housing 110 or in a through channel of the housing 110 (e.g., by adhesive, thermoplastic, or a connecting member), or the inner cannula section 121 may also be integrally formed with the inner wall of the housing 110 or the through channel of the housing 110. In this way, the structure of the single-port surgical device 100 can be simplified, and the mutual movement between the plurality of cannulas 120 can also be avoided. In some embodiments, the inner cannula section 121 and the outer cannula section 122 may comprise tube sections made of a flexible material and tube sections made of a non-flexible material, and the tube sections made of the flexible material and the tube sections made of the non-flexible material may be alternately distributed in a lengthwise direction of the inner cannula section 121 and the outer cannula section 122 based on functional requirements and design requirements (i.e., taking into account the process or cost). A part of the inner cannula section 121 extending toward the distal port 112 is made of a non-flexible material, which can ensure the alignment of communication between an end of the cannula 120 and the distal port 112 of the housing 110. At least a portion of the outer cannula section 122 is made of a flexible material, so that the outer cannula section 122 of the cannula 120 is deformable.

It should be understood that in any embodiment of the present disclosure, the flexible material may include thermoplastic elastomer (such as thermoplastic polyurethane), silicone or rubber, etc. The non-flexible material may include plastic (such as polycarbonate and polypropylene) or a metal material, etc.

In some embodiments, as shown in FIGS. 1 to 4, the at least one cannula 120 may comprise a plurality of cannulas. For example, the at least one cannula 120 may comprise, but is not limited to, two cannulas, three cannulas or more cannulas, and the specific number of cannulas may be adjusted according to actual requirements. The outer cannula section of at least one cannula of the plurality of cannulas 120 is deformable. It should be understood that the outer cannula section/sections 122 of one, several or all of the plurality of cannulas 120 is/are deformable. FIG. 6 is a partial sectional schematic structural diagram of a single-port surgical device 100 according to some embodiments of the present disclosure. In some embodiments, as shown in FIG. 6, at least one cannula 120 may comprise cannulas 120a, 120b, and 120c. In some embodiments, as shown in FIG. 6, outer cannula sections of the cannulas 120a and 120b may be flexible and deformable, and inner cannula sections thereof may be rigid. An outer cannula section and an inner cannula section of the cannula 120c may be non-flexible. In some embodiments, the cannula 120c may be used for a surgical instrument (e.g., an endoscope) to pass through.

As shown in FIG. 6, the inner cannula sections 121a-c of the cannulas 120a-care disposed adjacent to each other at the ends thereof close to the distal port 112 at the distal end of the housing 110, and may be away from each other at the end thereof close to the proximal port 111 at the proximal end of the housing 110, thereby better avoiding interference and collision of the plurality of motion arms when passing through the plurality of cannulas. In some embodiments, the cannulas 120a-c may have different lengths. As shown in FIG. 6, the length of the cannula 120c may be less than those of the cannulas 120a and 120b, so as to facilitate extension of the surgical instrument (e.g., the endoscope) into a surgical site. It should be understood that the cannulas 120a-c may also have the same length, or some of the cannulas have the same length. In some embodiments, as shown in FIG. 5, the inner cannula sections 121 of the plurality of cannulas 120 may also be disposed spaced apart from and parallel to each other in a lengthwise direction of the housing 110. In some embodiments, the outer cannula sections 122 of the plurality of cannulas 120 may also extend gradually outward away from each other.

In some embodiments, the outer cannula section 122 of the at least one cannula 120 may comprise a telescopic tube 130, as shown in FIGS. 5 and 6. The telescopic tube 130 is capable of telescopically moving in the axial direction of the outer cannula section 122 to deform the outer cannula section 122 in the axial direction, increasing the flexibility of the cannula 120 in the axial direction. In some embodiments, as shown in FIGS. 5 and 6, the telescopic tube 130 is tubular, and may comprise an upper tube 131 and a lower tube 132 which can slide relative to each other in the axial direction of the outer cannula section 122. The upper tube 131 and the lower tube 132 may have different diameters, and the upper tube 131 and the lower tube 132 are movably sleeved together to implement extending or retracting of the telescopic tube 130 in the axial direction. It should be understood that the telescopic tube 130 may communicate with and be disposed at any position on the outer cannula section 122 of the cannula 120. For example, as shown in FIGS. 5 and 6, the telescopic tube 130 may be disposed at a proximal end of the outer cannula section 122. A lower end part of the lower tube 132 is fixedly connected to an end portion of the outer cannula section 122, and the diameter of the upper tube 131 is greater than that of an upper end part of the lower tube 132, so that the upper tube 131 can be movably sleeved on the upper end part of the lower tube 132, to implement the relative sliding of the two in the axial direction of the outer cannula section 122. In some embodiments, the upper tube 131 and/or the lower tube 132 may be provided with a stop (not shown) to prevent the upper tube 131 and the lower tube 132 from slipping off during relative sliding. In some embodiments, the lower end part of the lower tube 132 may comprise a protruding portion 1321 extending outward in the radial direction, and the diameter of the protruding portion 1321 is greater than that of the other part of the lower tube 132. It may be understood that although the protruding portion 1321 is shown as being disposed on the lower tube 132 in FIGS. 5 and 6, the protruding portion 1321 may also be disposed at another position on the outer cannula section. In some embodiments, the protruding portion 1321 of the lower tube 132 may comprise an inner cavity, a sealing member 1322 may be disposed in the inner cavity, and the sealing member 1322 is provided with a cutout for the surgical instrument to pass through. When the surgical instrument passes through the cannula 120 and moves relative to the cannula 120 by means of the sealing member 1322, the cannula 120 may be kept in a sealed state to meet the requirements of surgical procedures, which, for example, may prevent collapse of the surgical site due to air leakage which affects the surgical field of view.

In some embodiments, as shown in FIGS. 2 and 5, the single-port surgical device 100 may be covered with a sealing cover 140 at the proximal port 111 of the housing 110, the sealing cover 140 may comprise at least one cutout, and the at least one cannula 120 can pass through the sealing cover 140 by means of the at least one cutout. In some embodiments, the sealing cover 140 is deformable, may be made of a flexible material, or may be implemented by movable assembly of a rigid material, and may provide a deformation amount including but not limited to that in the radial direction of the proximal port 111 and/or perpendicular to the radial direction of the proximal port 111, so as to improve the flexibility of the cannula.

In some embodiments, as shown in FIGS. 1 to 4, the single-port surgical device 100 may further comprise at least one connecting member 150. The connecting member 150 may be disposed on the housing 110 and/or the cannula, and the connecting member 150 is configured to connect a motion arm or a surgical instrument clamped on the motion arm to the single-port surgical device 100. In some embodiments, the connecting member 150 may comprise a protrusion, which is used for matching pincers mounted on the motion arm. In some embodiments, the connecting member 150 may also include pincers, a snap-fit structure, an adhesive structure, a pluggable structure, a suction structure, etc. The motion arm may comprise a structure matching the connecting member 150. The connecting member 150 may be disposed on the cannula 120 (e.g., the outer cannula section 122), and the connecting member 150 may be detachably and fixedly connected to the motion arm, so that the surgical instrument disposed on the motion arm can smoothly pass through the cannula 120 at a predetermined angle and move along the cannula 120. In some embodiments, the connecting member 150 may also be disposed on the telescopic tube 130 (e.g., the upper tube 131), and the connecting member 150 is capable of telescopically moving in the axial direction of the cannula 120 together with the telescopic tube 130, so that the flexibility of the position of the connecting member 150 on the cannula 120 can be improved to facilitate connection between the connecting member 150 and the motion arm.

In some embodiments, as shown in FIGS. 1 and 2, at least one side tube 113 may be disposed on the housing 110, and the side tube 113 may penetrate from an outer side wall of the housing 110 to an inner side wall of the housing 110 and communicate with the distal port 112. The side tube 113 may include an air tube or an instrument tube, and the air tube may be configured to inflate a body (e.g., a cavity of a person or an animal) connected to the housing 110 to facilitate a surgical operation. The instrument tube may be used for an auxiliary instrument (e.g., a clamping instrument for assisting a doctor or a nurse) to pass through, so as to perform an auxiliary surgical operation. In some embodiments, two side tubes 113 may be in, but are not limited to, distribution spaced apart from each other in a circumferential direction of the cannula, e.g., symmetrical distribution in the circumferential direction of the cannula.

The present disclosure further provides a medical device system, comprising at least one motion arm, at least one surgical instrument disposed at the end of the at least one motion arm, a control system, and a single-port surgical device in any one of the foregoing embodiments. FIG. 7 is a schematic structural diagram of a motion arm 10 of a medical device system according to some embodiments of the present disclosure. In some embodiments, as shown in FIG. 7, the motion arm 10 may comprise a plurality of arm bodies and a plurality of joints connecting the plurality of arm bodies. The surgical instrument 20 may comprise a surgical instrument arm body 21 and an end device 22 disposed at a distal end of the surgical instrument arm body 21. The end device 22 may include, but is not limited to, a pair of surgical forceps, an electrotome, an electric hook, an imaging device, and a lighting device, etc. At least a portion of the single-port surgical device (e.g., a part of the housing 110 close to the distal end or at least a portion of the inner cannula section 121 of the single-port surgical device 100) is used to extend into a patient's body, and a part of the single-port surgical device 100 exposed outside the patient's body (e.g., a part of the housing 110 close to the proximal end or the outer cannula section 122) may be configured to be connected to the motion arm 10.

FIG. 8 is a schematic structural diagram of a medical device system 1000 according to some embodiments of the present disclosure. As shown in FIG. 8, the medical device system 1000 may comprise a plurality of motion arms 10. A control system is configured to control the movement of the plurality of motion arms 10, so that the plurality of motion arms 10 move to an appropriate position (e.g., a target position and posture), so as to facilitate connection to the single-port surgical device. When the motion arms 10 cannot precisely move to the target position and posture for some reasons, an in-position error exists between the actual position and posture which the motion arms 10 can reach and the target position. In this way, the deformation of the outer cannula section 122 of the cannula 120 of the single-port surgical device (e.g., the single-port surgical device 100) can compensate for the in-position error of the motion arm 10, so that the motion arm 10 can still be smoothly connected to the single-port surgical device 100 and the end device 22 at a distal end of the surgical instrument 20 can smoothly enter a predetermined surgical site by means of the cannula 120 and the inner cavity of the housing 110 even in the situation in which there is a certain in-position error.

In some embodiments, as shown in FIGS. 7 and 8, the motion arm 10 may comprise an end arm 11, and the end arm 11 may be configured to be connected to the surgical instrument 20. In some embodiments, the end arm 11 may comprise a linear module which slides in a lengthwise direction of the end arm 11, and the surgical instrument 20 is detachably and fixedly connected to the linear module. The linear module can drive the surgical instrument 20 to slide in the lengthwise direction of the end arm 11, so that the surgical instrument 20 moves along the cannula 120 of the single-port surgical device 100. Each of the end arms 11 of the plurality of motion arms 10 can be detachably connected to the single-port surgical device 100, and at least a portion of each of the plurality of surgical instruments 20 (e.g., the end device 22 and a distal part of the surgical instrument arm body 21) can pass through the at least one cannula 120 of the single-port surgical device 100, and move relative to the single-port surgical device 100 or move together with the single-port surgical device 100 with the relative position and posture therebetween unchanged.

It should be noted that the foregoing descriptions are merely exemplary embodiments of the present disclosure and technical principles applied thereto. Those skilled in the art can understand that the present disclosure is not limited to the specific embodiments herein, and various obvious modifications, changes and substitutions can be made by those skilled in the art without departing from the protection scope of the present disclosure. Therefore, the present disclosure is described in detail by the foregoing embodiments, but the present disclosure is not limited to the foregoing embodiments. Other equivalent embodiments may also be included without departing from the concept of the present disclosure. Therefore, the scope of the present disclosure depends on the appended claims.

The invention claimed is:

1. A single-port surgical device for connecting to a plurality of motion arms of a medical device system, the single-port surgical device comprising:

a housing comprising a proximal port formed as a bell mouth and a distal port formed as a contraction port; and a plurality of cannulas each comprising an inner cannula section and an outer cannula section, wherein the inner cannula section is located in the housing and communicates with the distal port of the housing, the outer cannula section is located outside the proximal port of the housing, and at least a portion of the outer cannula section of at least one of the plurality of cannulas is deformable in a radial direction, an axial direction or the radial direction and the axial direction of the outer cannula section;

wherein the inner cannula sections of the plurality of cannulas are close to each other in a direction from the proximal port to the distal port so as to be disposed adjacent to one another at the ends thereof close to the distal port and away from one another at the end thereof close to the proximal port, wherein the outer cannula sections of the plurality of cannulas extend outwardly away from one another, wherein the inner cannula sections of the plurality of cannulas are fixedly connected to an inner wall of the housing or integrally formed with the housing to form a plurality of fixed rigid channels, so as to avoid relative movements therebetween; and wherein the single-port surgical device further comprises a plurality of connecting members for detachably and fixedly connecting to the plurality of motion arms of the medical device system respectively, wherein the plurality of connecting members are respectively disposed on the housing and the outer cannula sections of the plurality of cannulas or respectively disposed on the outer cannula sections of the plurality of cannulas.

2. The single-port surgical device according to claim 1, wherein at least a portion of the outer cannula section of at least one of the plurality of cannulas comprises a flexible material.

3. The single-port surgical device according to claim 2, wherein the flexible material includes thermoplastic elastomer, silicone or rubber.

4. The single-port surgical device according to claim 1, wherein at least a portion of the inner cannula section or the outer cannula section of the plurality of cannulas comprises a non-flexible material.

5. The single-port surgical device according to claim 4, wherein the non-flexible material includes plastic or a metal material.

6. The single-port surgical device according to claim 1, wherein the plurality of cannulas comprise at least one non-flexible cannula.

7. The single-port surgical device according to claim 1, wherein the outer cannula section of the plurality of cannulas comprises a telescopic tube, and wherein each telescopic tube is capable of telescopically moving in the axial direction of the outer cannula section to deform the outer cannula section in the axial direction.

8. The single-port surgical device according to claim 7, wherein each telescopic tube comprises an upper tube and a lower tube which are sleeved with each other and capable of sliding relative to each other.

9. The single-port surgical device according to claim 8, wherein each lower tube comprises a protruding portion extending outwardly in the radial direction, the protruding portion comprises an inner cavity and a sealing member disposed in the inner cavity, and the sealing member comprises a cutout.

10. The single-port surgical device according to claim 1, wherein each outer cannula section comprises a protruding portion extending outwardly in the radial direction, the protruding portion comprises an inner cavity and a sealing member disposed in the inner cavity, and the sealing member comprises a cutout.

11. The single-port surgical device according to claim 1, further comprising a sealing cover disposed at the proximal port of the housing, wherein the sealing cover is deformable and comprises a cutout.

12. The single-port surgical device according to claim 1, wherein each connecting member includes at least one of a protrusion, pincers, a snap-fit structure, an adhesive structure, a pluggable structure, or a suction structure.

13. The single-port surgical device according to claim 1, wherein at least one side tube is disposed on the housing, and the at least one side tube passes through a side wall of the housing and communicates with the distal port.

14. The single-port surgical device according to claim 13, wherein the at least one side tube comprises a first side tube and a second side tube which are spaced apart from each other in a circumferential direction of the housing.

15. A medical device system, comprising:

a plurality of motion arms each comprising a plurality of arm bodies and a plurality of joints connecting the plurality of arm bodies;

a plurality of surgical instruments respectively disposed at ends of the plurality of motion arms, each surgical instrument comprising an end device disposed at an end thereof;

a control system in communication with the plurality of motion arms and for controlling the movement of the plurality of motion arms; and a single-port surgical device comprising: a housing, the housing being tubular and comprising a proximal port formed as a bell mouth and a distal port formed as a contraction port; a plurality of cannulas for the plurality of surgical instruments to pass through, each of the plurality of cannulas comprising an inner cannula section and an outer cannula section, wherein the inner cannula section is located in the housing and communicates with the distal port of the housing, the outer cannula section is located outside the proximal port of the housing, and at least a portion of the outer cannula section of at least one of the plurality of cannulas is deformable in a radial direction, an axial direction or the radial direction and the axial direction of the outer cannula section;

wherein the inner cannula sections of the plurality of cannulas are close to each other in a direction from the proximal port to the distal port so as to be disposed adjacent to one another at the ends thereof close to the distal port and away from one another at the end thereof close to the proximal port, wherein the outer cannula sections of the plurality of cannulas extend outwardly away from one another, wherein the inner cannula sections of the plurality of cannulas are fixedly connected to an inner wall of the housing or integrally formed with the housing to form a plurality of fixed rigid channels, so as to avoid relative movements therebetween; and wherein the single-port surgical device further comprises a plurality of connecting members for detachably and fixedly connecting to the plurality of motion arms respectively, wherein the plurality of connecting members are respectively disposed on the housing and the outer cannula sections of the plurality of cannulas or respectively disposed on the outer cannula sections of the plurality of cannulas.

16. The medical device system according to claim 15, wherein the plurality of motion arms comprise a plurality of end arms, wherein the plurality of motion arms are configured to detachably connect to the plurality of surgical instruments respectively and to detachably connect to the plurality of connecting members of the single-port surgical device respectively, and wherein at least a portion of the plurality of surgical instruments are respectively capable of passing through the plurality of cannulas of the single-port surgical device and moving relative to the single-port surgical device.

* * * * *